United States Patent [19]

Stangl et al.

[11] Patent Number: 5,645,575

[45] Date of Patent: Jul. 8, 1997

[54] CARDIAC PACEMAKER AND PACING METHOD USING DETECTION OF PHYSICAL STRESS FOR ADJUSTING STIMULATION RATE

[75] Inventors: Karl Stangl; Michael Laule; Roland Heinze, all of Berlin, Germany

[73] Assignee: Pacestetter AB, Solna, Sweden

[21] Appl. No.: 576,755

[22] Filed: Dec. 21, 1995

[30] Foreign Application Priority Data

Dec. 29, 1994 [DE] Germany .................. 44 47 447.4

[51] Int. Cl.$^6$ ............................................. A61N 1/362
[52] U.S. Cl. ............................................. 607/17
[58] Field of Search ...................... 607/17, 18, 19, 607/20, 21, 27

[56] References Cited

U.S. PATENT DOCUMENTS 4,873,980  10/1989  Schaldach .................. 607/18
5,360,436  11/1994  Alt et al. .................... 607/18

FOREIGN PATENT DOCUMENTS 299208  1/1989  European Pat. Off. .

Primary Examiner—Scott M. Getzow
Attorney, Agent, or Firm—Hill, Steadman & Simpson

[57] ABSTRACT

In a method and apparatus for operating an implantable cardiac pacemaker, the stimulation rate is modulated, while a patient in whom the pacemaker is implanted is experiencing a number of different levels of physical stress, and a number of signal sequences corresponding to a non-mechanical physiological characteristic are obtained, one sequence being obtained for each physical stress level. These signal sequences form a reference field, which is stored in the pacemaker. A current signal sequence of the non-mechanical physiological characteristic is subsequently obtained, and this signal sequence is compared to all of the signal sequences in the stored reference field, and one of the reference field signal sequences having the highest correlation with the current signal sequence is selected. The stimulation rate is then set at a rate equal to the basic stimulation rate for the modulation which produced the highest correlating sequence in the reference field.

42 Claims, 4 Drawing Sheets

CARDIAC PACEMAKER AND PACING METHOD USING DETECTION OF PHYSICAL STRESS FOR ADJUSTING STIMULATION RATE

BACKGROUND OF THE INVENTION

1. Field of the Invention

The present invention is directed to a pacemaker having the capability of detecting physical stress in a patient in whom the pacemaker is implanted in order to adjust the stimulation rate, as necessary dependent on the detected physical stress, as well as to a method for operating a pacemaker for achieving such adjustment.

2. Description of the Prior Art

A number of methods are known for adapting the stimulation rate of a heart pacemaker to the stress situation of the patient. A broad differentiation can be made between systems which use non-physiological parameters such as, for example, the movement (activity) of the body, and systems which use physiological parameters of the body such as, for example, blood pressure or blood temperature, for stimulation rate. Non-physiological rate-adaptive systems have the disadvantage that they can lead to stimulation rates which are not accurately matched to actual cardiac demand (upstairs-downstairs-paradox). Physiologically regulating sensors have the disadvantage that they require special sensors to measure suitable regulating parameters of the cardiac circulatory system, and these sensors do not have long-term stability. For this reason a number of processing augmentations, as well as non-specific measurement procedures, have to be carried out with standard catheters having long-term stability, such as intracardial impedance measurement for the heart pacemaker and defibrillator control. A significant feature of these known processing augmentations is the use of special methods in order to filter the signal content out of the polymorphic signal, this signal content in turn being clearly assigned to physiologically definable occurrences. A differentiation is made between two concepts:

1. Passive measurement of intracardial and intrathoracic measurement values without intentional influence of the measurement path by the stimulator.
2. Active measurement of intracardial measurement parameters with defined influence of cardiovascular functions by the stimulator.

Active measuring systems, such as those operating through modulation of the stimulation rate of the heart muscle, have the advantage of suppressing non-cardiac disturbance by phase-synchronous analysis, and are preferred for the use of physiological function parameters for frequency regulation.

In the case of active measuring systems, it is known to use signal evaluation, related to frequency change, of action parameters of the heart to analyze intracardial impedance signals for rate regulation in heart pacemakers as described, for example, in U.S. Pat. No. 5,360,436. In this context, efforts have been made to evaluate the signal configuration of an intracardial measurement parameter during a heart pulse (n+1) dependent on frequency changes $\Delta HR$ of a single preceding pulse (n). It has also been proposed to use the difference in the signal alterations of two successive pulses (n+1) and (n+2) dependent on the frequency of the first pulse (n). In order to standardize the individual or difference values, a quotient is calculated from the respective measurement value and a maximum change value determined at a higher frequency change. A substantial disadvantage of this arrangement is that this method is only successful with measurement signals at which an exact separation is possible between volume-caused and pressure-caused changes. This is, however, difficult in the case of conventional impedance measurement using a single-pole catheter because, in addition to the shape and volume of the ventricle, pressure changes at the electrodes significantly influence the signal configuration. In order to compensate for these influences it is necessary in setting up the system to carry out a separation of the pressure- and volume-dependent signal components. The disclosure of the aforementioned patent, however, gives no indication of how this separation is to be accomplished.

It is further known to optimize the rate regulation by means of periodic alteration of the stimulation rate, causing alterations in the cardiac volume or per given time unit to occur synchronously with the frequency alterations, with measurements thereof then being evaluated. This known procedure has the disadvantage that the time-constant of measurement of the cardiac volume with the required precision increases in such a way that optimization is only possible in long phases of uniform stress, i.e. no short-term adaptations to stress can be carried out (German OS 38 03 473).

SUMMARY OF THE INVENTION

It is an object of the present invention to provide an arrangement for detecting physical stress for use in controlling the stimulation rate in a heart pacemakers, which, without the need to filter out function-specific signal components from an intracardial mixed measurement signal, detects the physical stress condition rapidly and precisely.

The above object is achieved in accordance with the principles of the present invention in a method and an apparatus wherein emission of stimulation pulses by a pulse generator is controlled by a regulator unit which sets a pulse interval between successive stimulation pulses and which, for the purpose of generating a reference field, modulates the stimulation rate by changing the pulse interval in a number of different modulation sequences, each modulation sequence starting from a base stimulation rate. A sequence of cardiac demand-indicative signals is obtained while the modulation is occurring with the patient in whom the cardiac pacemaker is implanted experiencing different levels of physical stress, with one sequence of cardiac demand-indicative signals being obtained for each different level of physical stress. The reference field is stored. Subsequently, as often as desired, a current sequence of the cardiac demand-indicative signals is obtained, this current sequence being compared to all of the sequences stored in the reference field. One of these stored sequences is identified as having the highest correlation with the current sequence. The pulse interval regulator then causes the pulse generator to emit stimulation pulses at a stimulation rate which is equal to the base stimulation rate which was used to produce the sequence in the reference field having the highest correlation with the current sequence.

The method and apparatus according to the invention circumvent the problem of filtering individual function-specific signal components out of d mixed signal such as intracardial impedance, abandoning exact discrimination and instead only analyzing sequences of specific signal parameters, which react in a precisely reproducible way to the magnitude of specific influences, such as, for example, physical stress and pulse rate of the heart, so that each sequence of values has a specific behavior curve depending an stress and rate. This provides the possibility, by storage of a number of these value sequences obtained with the patient experiencing known stresses as a field of reference values, to compare one or more current value sequences with the stored values, thereby of detecting the current level of stress. The stored value sequence is ascertained which in relation to the respective base rate, has the highest correlation with the present value sequence. This procedure does not need any precise analysis of individual stress-produced signal contents.

In a preferred embodiment of the method and apparatus, a field of reference values is associated with each previously selected (known) combination of specific stress condition and pulse frequency the field of reference values, being a sequence of signal parameters of physiological measurement signals which are stored. These stored values are then used as reference magnitudes (pattern-template) in order to detect various stress situations by means of a comparison with current measurement signal sequences or patterns. The effectiveness of the procedural principle used herein, that of identification of configuration characteristics or configuration patterns of physiological measurements, increases dependent or the extent to which disturbances can be reduced when the respective value sequences are obtained, thus making their respective configuration more characteristic of particular physiological conditions. The precisely reproducible value patterns or the reference value fields are obtained by modulating a set stimulation rate and using as a signal parameter only those signal components which are influenced by the rate modulation, so that by means of demodulation, disturbances unsynchronized with the modulation rate are suppressed. An exemplary method of obtaining a sequence of signal parameters is to proceed through various types and degrees of rate modulation, whereupon, with subsequent demodulation, a correspondingly large number (sequence) of values may be obtained.

It is a particular advantage of the method and apparatus of the invention that a rapid and precise regulation of the stimulation rate may be matched to the current stress condition.

DESCRIPTION OF THE PREFERRED EMBODIMENTS

Figure 4:
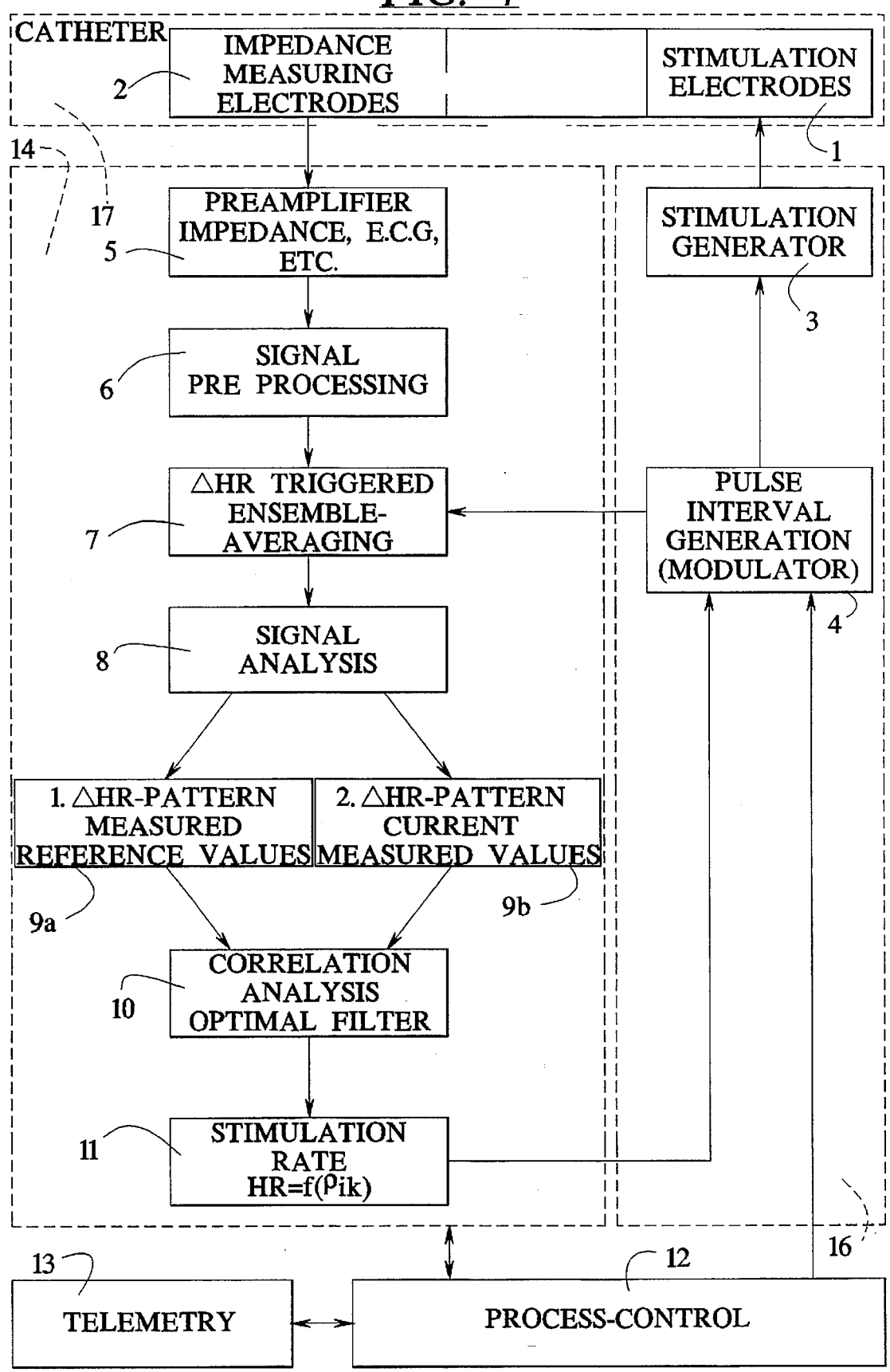
FIG. 4 is a block diagram of a cardiac pacemaker constructed and operating in accordance with the principles of the present invention.

FIG. 4 shows a block diagram of a heart pacemaker, which is controlled to emit stimulation pulses at a presettable stimulation rate. The heart pacemaker includes a stimulation pulse generator 3, which is connected to a cable 17 carrying one or more electrodes located in the heart of the patient via which the stimulation pulses are delivered to cardiac tissue (multiple cables 17 also being possible). The stimulation pulse generator 3 is connected to a regulation stage 4. which controls the magnitude and chronological sequence (i.e. the rate) of the stimulation of pulses. The stimulation electrodes 1 are simultaneously used as measuring electrodes for ECG and impedance measurement, additional sensors 2 (for example for measuring pressure or oxygen content) being also integrated in the cable 17. The electrodes 1 and sensors 2 are connected to a processing and evaluating unit 14, in which the signals provided by the electrodes 1 or sensors 2, as will be described later, are processed and evaluated. The processing and evaluation unit 14 is connected to a standard operational control system 12 and a telemetry device 13, which transmits data from the processing unit 14 to, and receives data and instructions from an external programmer (not shown). The heart pacemaker is controlled to emit stimulation pulses via the stimulation electrodes 1 at a stimulation rate pre-established by the regulation stage 4. This rate is set in dependence on different setting parameters by the regulating stage 4. Table 1 shows the most common setting parameters for stimulation rate ($HR_o$), along with their changes ($\Delta HR_j$) from which, depending on the particular application, specific combination sequences or patterns may be assembled. In the bottom row of Table 1 the number of a normal combination, and in brackets that of a maximum combination, of cases is given.

TABLE 1

| SETTING PARAMETERS OF THE STIMULATION RATE ($HR_o$, $\Delta HR_j$) | | | |
|---|---|---|---|
| Type of stimulation (SM) | Basic value of pulse rate ($HR_o$) | Type of rate modulation (FM) | Degree of rate modulation ($\Delta HR$) |
| Pacing | | | |
| 1. ventricle (2. Atrium) (3. A/V) 4. | 1. 60–80 P/min 2. 80–100 P/min 3. 100–130 P/min 4. 130–160 P/min | 1. single pulse positive (+$\Delta HR$) (2. single pulse negative (–$\Delta HR$)) 3. double pulse ($\pm\Delta HR$) | 1. 5% 2. 10% 3. 20% (4. 40%) |
| 2 (4) | 1–8 (1–16) | 2 (3) | 1–6 (1–12) |

Under type of stimulation SM there is in principle a distinction between intrinsic rhythm (SINE) and artificial stimulation, which is in turn separated into the atrium (A), ventricle (V), and the combined (A–V) stimulation. There are firstly determined, as basic values (basic rate $HR_o$) of the stimulation rate, only four values which have respectively been selected from a value range which in turn is associated with one of the stress ranges defined in the following. During SINE rhythm, the respective average pulse frequency of several (>4) successive pulses is calculated as a reference magnitude and is assigned to one of the four rate ranges.

As is known, for rate regulation of the stimulation rate, the latter is modulated, and, for example by means of ECG measurement, the reactions of the intracardial signals to this modulation are detected and evaluated. Thus the type of rate modulation and the degree of rate modulation, or both, may be altered. In accordance with Table 1, in the types of modulation, a differentiation is made, only as an example, between typical forms of single pulse modulation, in which at a periodical interval of n pulses the interval between two successive pulses is either extended ($-\Delta HR_j$) or abbreviated ($+\Delta HR_j$). Other types of rate modulation may naturally also be considered; for reasons of simplicity the embodiment relates to double-pulse modulation.

In Table 1, the degree of rate modulation is given in percent, the reference magnitude being the basic rate $HR_o$ of the stimulation pulses. For a gradually graded setting of the degree of modulation, abbreviations or extensions of the pulse interval are selected which correspond to a rate differential of ±5, 10 and 20%.

Table 2 shows the setting parameters for physical stress $P_k$. As examples, various types of physical stress are entered, which are used in the medical field for the assessment of body functions as reproducible stress conditions. Accordingly such stress settings, in conjunction with defined rate modulations, can supply reference values which are required for general stress detection in heart pacemakers. The degree of physical stress is different for different persons, therefore for the individual person firstly the maximum performance level ($N_{max}$) first must be determined, which serves as a reference magnitude for example for two further stress stages with ⅓ and ⅔ $N_{max}$.

TABLE 2

SETTING PARAMETERS FOR PHYSICAL STRESS ($P_K$)

| TYPE of Physical Stress | DEGREE of Physical Stress |
|---|---|
| 1. Sitting (bicycle ergometer) | 1. Rest |
| (2. Lying) | 2. ⅓ $N_{MAX}$ (W) |
| (3. Walking (treadmill)) | 3. ⅔ $N_{MAX}$ (W) |
|  | 4. 1 $N_{MAX}$ (W) |
| 1 (3) | 1–4 (1–12) |

The basis of the inventive idea resides in the fact that, for an individual person, fields of measurement values at alterable stress stages or degrees and at different stimulation rates are stored, and serve as reference value fields, to which current measurements may be compared, the result of the comparison being usable for control or regulation of the stimulation rate. Thus the type of intracardial signals underlying the measurement values may be selected arbitrarily, with only those respective same signal parameters then being used in the obtaining of the reference value fields and in the current measurement values.

The type of set-up of the reference value fields will be explained in more detail in the following. Table 3 shows a stress-stimulation rate (basic rate)-coordinate field (HR-P-coordinate field) having physical stress levels or ranges $P_k$ in the left vertical column and pulse rates in $HR_j$ on the top row, pair is a sequence of measurement values $M_{ik}$ ($\Delta HR_j$) this sequence of measurements, i.e. of intracardial measurement signals, being determined in dependence on the respective degree of rate modulation ($\Delta HR_j$). Thus there arises the exemplary arrangement of values assembled in Table 3.

TABLE 3

| Pulse Rate Stress | $HR_1$ | $HR_2$ | $HR_3$ | ... | ... | $HR_{jmax}$ |
|---|---|---|---|---|---|---|
| $P_1$ | $M_{11}$ ($\Delta HR_j$) | $M_{12}(\Delta HR_j)$ | $M_{13}(\Delta HR_j)$ |  |  | $M_{1,imax}$ ($\Delta HR_j$) |
| $P_2$ | $M_{21}$ ($\Delta HR_j$) | $M_{22}(\Delta HR_j)$ | $M_{23}(\Delta HR_j)$ |  |  | $M_{2,imax}$ ($\Delta HR_j$) |

TABLE 3-continued

| Pulse Rate Stress | $HR_1$ | $HR_2$ | $HR_3$ | ... | ... | $HR_{jmax}$ |
|---|---|---|---|---|---|---|
| ... |  |  |  |  |  |  |
| ... |  |  |  |  |  |  |
| $P_{kmax}$ | $M_{kmax,1}$ ($\Delta HR_j$) | $M_{kmax,2}$ ($\Delta HR_j$) | $M_{kmax3}$ ($\Delta HR_j$) |  |  | $M_{kmax,imax}$ ($\Delta HR_j$) |

In order to determine the reference value field in the present embodiment, an HRP-coordinate field is determined with four basic values ($HR_o$) for the stimulation (pulse) rate, and four values ($P_k$) for the physical stress situation, giving rise to 16 event fields. Associated with each of these fields is a sequence of measurements $M_{ik}$, which in the present case are calculated as a function of various stages of rate modulations ($\Delta HR_j$).

As rate modulation, a constant type of modulation can be used at which a combination is selected of an equal-sized positive and negative rate alteration of two successive pulse intervals (double-pulse modulation), and on the other hand three different degrees of modulation (dHR) of 5, 10 and 20% are used. Each rate alteration is repeated after a specific number of pulses, in order to be able to form an average value over a specific number of pulses (m), at the modulation degree of S% a number $m_5=16$, at the modulation degree of 10% $m_{10}=12$ and at the modulation degree of 20% $m_{20}=8$ are chosen.

Figure 1:
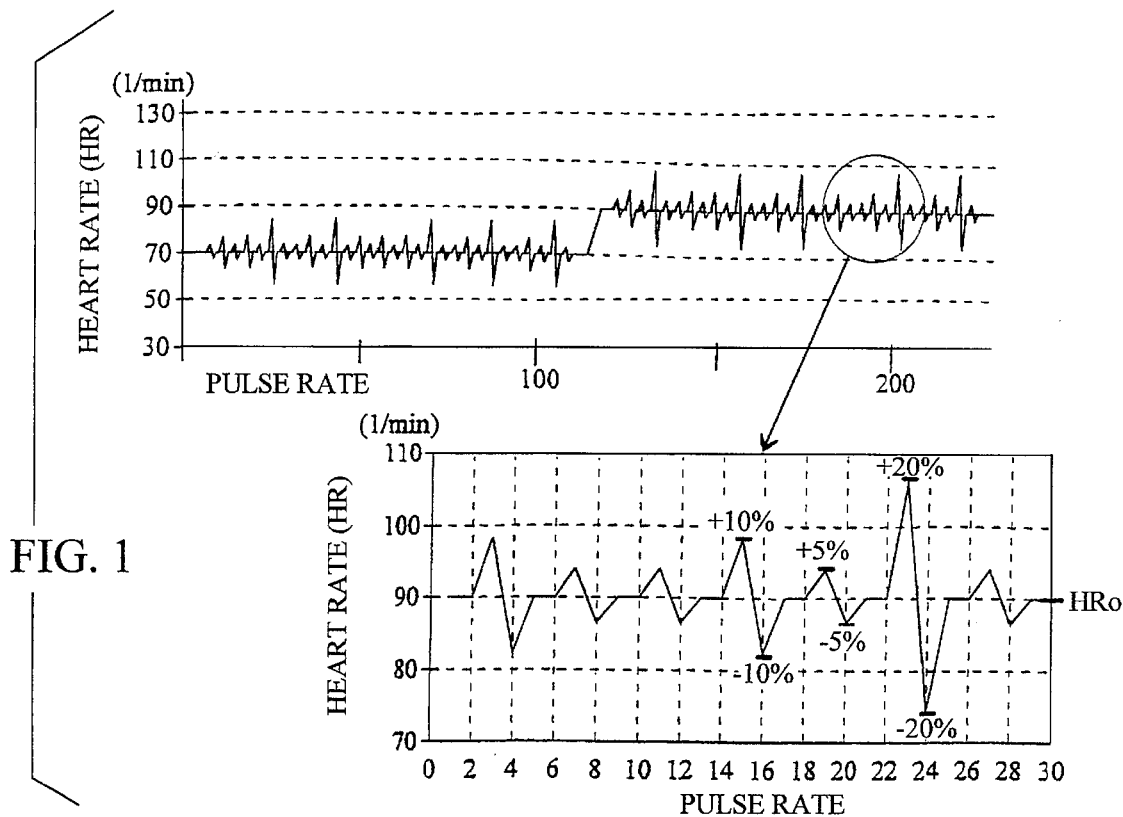
FIG. 1 illustrates a chronological configuration of the modulated stimulation rate at different basic rates and different degrees of modulation with double-pulse modulation in accordance with the principles of the present invention.

If, between the individual grades and double pulse modulations, two unmodulated pulse intervals ($HR=HR_o$) are used, the chronological configuration of the modulated stimulation or pulse rate at two different basic values $HR_o$ (70 and 90 pulses/minute) results as shown in FIG. 1. As may be seen from FIG. 1, the lower modulated pulse intervals have a higher repetition rate, because signal alterations at a low degree of modulation logically have a lower disturbance interval and accordingly should be integrated over a higher number of pulses. Moreover, in the example shown, repetition rates are randomly variable in a specific range, in order to prevent interferences with periodic influences on the intracardial signal such as, for example, respiration.

In the embodiment described and illustrated, impedance is selected as a $\Delta HR_j$-dependent signal parameter, i.e., the average standardized (normalized) value $\alpha_{ik}$ of the maximum impedance change $dz_{max}$ during a pulse interval (n+1), after the interval alteration of the pulse (n). The average value $\Delta z_{max}$ was in this case calculated in accordance with the different rates above, for example, $m_5=16$, $m_{10}=12$ and $m_{20}=8$ (m number of pulses). Thus the following results for the respective average value:

$$\overline{\Delta Z_{max}}(\Delta HR_j) = 1/m \sum_{n=1}^{m} \Delta Z_{max(n)}$$

with $\Delta Z_{max(n)} = Z_{max(n)} - Z_{min(n)}$

The quotient is, for example, calculated as a standardized (normalized) value $\alpha_{ik}$ from the difference between the $dz_{max}$ value of the respective pulse (n+1), which is influenced by a rate alteration (dHR$_j$) of the preceding pulse interval (n), and a reference value ($dz_{omax+}$) which is not influenced by a rate alteration, $da_{omax}$ according to:

$$\alpha_{ik}(dHR_j) = (\overline{\Delta Z_{max}} \Delta Z_{omax}/\Delta Z_{omax}$$

Figure 2:
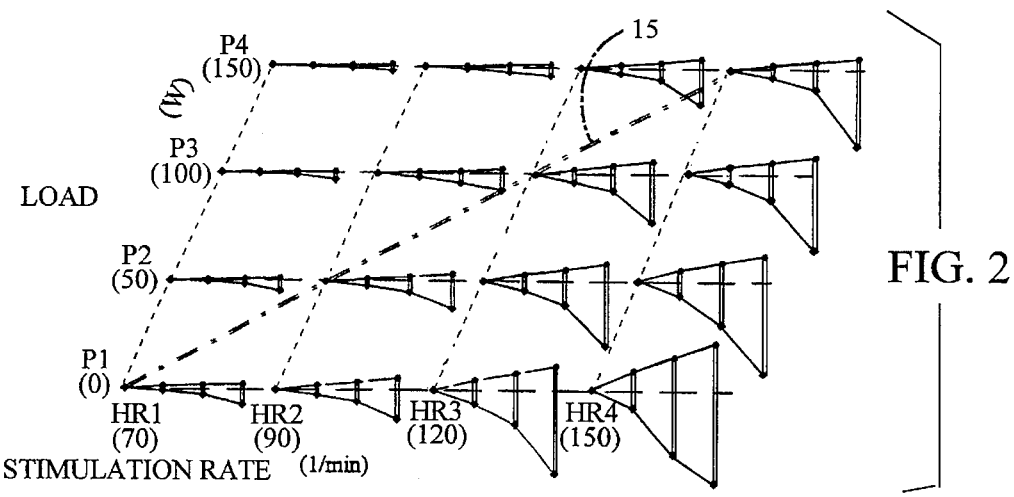
FIG. 2 illustrates a field of reference values as a stress stimulation rate-coordinate field with different basic rates and different stress stages in accordance with the principles of the present invention.

FIG. 2 shows an HR-P coordinate field, according to Table 3, as a reference value field of characteristic measurement sequences, in the form of standardized $\alpha_{ik}$ (dHR$_j$) sequences. The value sequences of six dHR-dependent signal parameters $\alpha_{ik}$ after RATE alterations with a modulation degree dHR of ±5, 10, 20%, were determined at four different basic RATES (70, 90, 120, 150 pulses per minute) and four stress stages (P1–P4) in accordance with Table 2. The value sequence $a_{31}$ at a basic rate of 120 pulses/minute in the resting condition is shown on an enlarged scale in FIG. 3, the fluctuations at the different degrees of modulation being clearly recognizable.

A reference value field such as is shown in FIG. 2, may be stored in a person-specific manner, naturally in addition or in place of it, further fields being storable with different parameters both as regards frequency modulation and also the stress as well as of the detected signal parameter.

According to the embodiment there are selected from the reference value field according to FIG. 2 during a defined stress test, i.e. in the reference measurement, the value patterns which result at the respective stimulation frequencies evaluated as optimal.

A physiologically optimal relation between stress and stimulation rate is described approximately by the equation $$HR_o + HR_{min} + c\, P_k,$$

HR$_o$ being the basic rate, and HR$_{min}$ and c being individually settable constants. From this there results for each basic frequency HR$_o$ an alteration pattern, defined as optimum, according to the characteristic curve 15 shown in dashed lines in FIG. 2, i.e. at four basic rates, four reference, value patterns. These reference value patterns are established in a person-specific manner. Should it prove advantageous for the patient, other reference value patterns may be selected from the entire reference value field, as appropriate to his or her physical condition.

In order to determine the current, unknown physical stress stage of the person in whom the heart pacemaker is implanted, as with the reference measurement, a standardized measurement sequence $\alpha_{ik}$ is determined at a pre-set basic frequency and at one type of rate modulation and various degrees of modulation, by measurement and calculation. In order to determine the physical stress stages with the aid of the currently-measured ΔHR-related value sequence, any suitable identification process can be used, the so-called optimum value of filtering being described in the embodiment. Thus the square of the average difference $(\Delta\alpha_{ik})^2$ between the values of the present measurement sequence and those of the reference value sequences is determined and the sum $\rho_{ik}$ of all such determined values is formed:

$$\rho_{ik} = \sum_{a=1}^{6} (\Delta\alpha_{ik})a^2 = \Sigma(\alpha_{ik} - \alpha_{ikref})a^2$$

It is generally true that the coordinate point for which $\rho_{ik}$ becomes smallest defines the current measurement sequence which correlates best with the reference value sequence, and thus characterizes the respective stress degree, i.e.

$$P_k = P_k\,(\rho_{ik} \to min.)$$

If $\rho_{ik}$ lies above a specific threshold value, regulation is carried out and the basic rate is increased or reduced in accordance with the value $\rho_{ik}$, and $\alpha_{ik}$ is measured and compared with the next higher or lower reference value pattern. In this way the optimum basic frequency for the current stress is set in accordance with the stored patterns.

The arrangement carrying out the processing procedure described above is shown in FIG. 4, the regulation stage 4 controlling the stimulation pulse generator with respect to magnitude and chronological sequence (rate) of the stimulation pulses being supplied to the stimulation electrodes 1.

The processing and evaluation unit 14 contains all the function stages necessary for processing the measurement signals derived from the sensors 2 or electrodes 1. These include at least one preamplifier 5 with A/D converter, a signal front-end (pre-processing) system 6, which is not related to pulse interval (i.e. stimulation rate), and a pulse-interval-triggered signal processing system 7. Upon alteration of the duration of the pulse interval, the frequency regulating stage 4 emits a test pulse to the processing stage 7, which then carries out the averaging. A subsequent signal analysis stage 8 detects the pulse interval-related values of the averaged signal configurations, which are the most characteristic for the respectively required analysis, such as, for example, the maximum amplitude alteration of the intracardial impedance per pulse interval. Subsequent to the signal analysis stage 8 is a memory stage 9, the reference value field or the reference fields being deposited in a memory area 9a, and the present measurement sequences being intermediately stored in a memory area 9b. A comparator stage 10 analyzes the correlation $\rho_{ik}$ between the reference value fields and the current measurement sequences and passes the result to the rate regulating stage 11. The basic value HR$_o$ of the stimulation rate, determined from the rate regulating stage 11 as a function of the correlation factor $\rho_{ik}$, controls the pulse interval of the regulator 4 in combination with the operation control system 12, which in turn, via the program predetermined by the telemetric system 13, the duration, type and degree of rate modulation.

In the embodiment described above, the measurement values with the form and configuration shown in FIG. 2 were determined on the basis of impedance measurement. Other measurement parameters, or combined parameters, however, may be selected, resulting in other forms of configuration underlying reference value fields from those shown in FIG. 2.

Adaptation of the heart pacemaker to altered stress conditions is relatively slow, as reactions to the modulation must be waited for, and the measurement cycle is relatively long. This may be improved by a combination with a movement-dependent sensor in accordance with FIG. 5.

Movement-dependent sensors are used in activity-controlled pacemakers, which, however, have the disadvantage that they are also in principle influenced by non-physiological magnitudes (acceleration, vibrations), and react in a non-specific way. Stress detection according to FIG. 5 enables a correction of non-physiological alterations to the stimulation rate.

Figure 5:
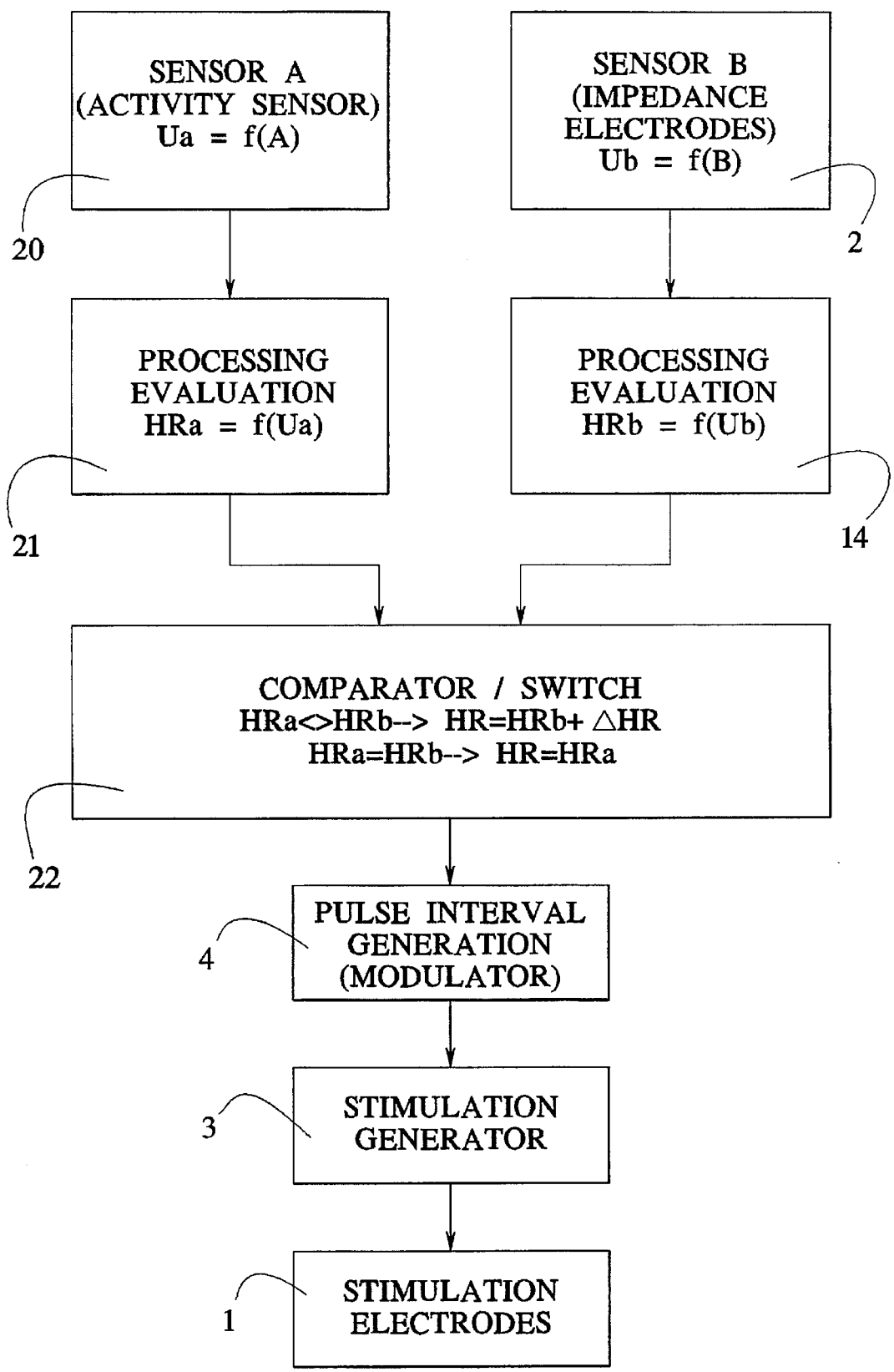
FIG. 5 is a block diagram of a further embodiment of a cardiac pacemaker constructed and operating in accordance with the principles of the present invention.

In the embodiment of the pacemaker shown in FIG. 5, a movement sensor 20 in the form for example of a piezoelement is provided, which is connected to a signal evaluation stage 21, whose output is connected to a comparator/switch 22, which is connected to the pulse regulator 4, which controls the stimulation pulse generator 3. The stimulation pulses are supplied to the stimulation electrodes 1.

The arrangement described above (FIG. 4) operates in parallel with the signals obtained from the movement sensor 20, i.e., via the impedance measurement 2, the impedance is measured and passed to the signal processing stage 14, which carries out processing of the detected measurement parameters, here the impedance, in comparison with the above-described stored reference values, and calculates the suitable stimulation rate $HR_b$ as a function of the current impedance values.

The device according to FIG. 5 operates as follows.

In a normal case, the basic frequency $HR_b$ is detected without carrying out modulation, and is controlled in accordance with the stimulation pulse generator 3, in a continuous manner and via the impedance sensor 2 and the signal processing stage 14. When the movement sensor 20 detects an altered movement, it is ascertained in the signal evaluation stage 21 whether the alteration lies above the pre-set threshold value and, as is known, a basic frequency $HR_b$ is assigned to the movement. In the comparator/switch 22 it is determined whether this basic rate is larger or smaller than the basic rate $HR_b$, which is continuously detected via the impedance measurement sensor 2.

If this is the case, a signal is emitted to the pulse interval emitter 4, to carry out a modulation $HR=HR_b+\Delta HR$, the stimulation pulse generator 3 emitting the corresponding pulses, and regulation is carried out according to the description with reference to FIGS. 1 to 4. In the comparator 22 it is ascertained whether the basic rate $HR_b$ determined via the signal processing stage 14 agrees with the rate $HR_1$ determined in dependence on the movement sensor if the alteration in movement was effected by non-physiological magnitudes, the pulse interval regulator 4 alters the basic rate to the value $HR_b$ set by means of via the impedance. Otherwise the basic rate $HR_1$ is used and the modulation is terminated.

Figure 3:
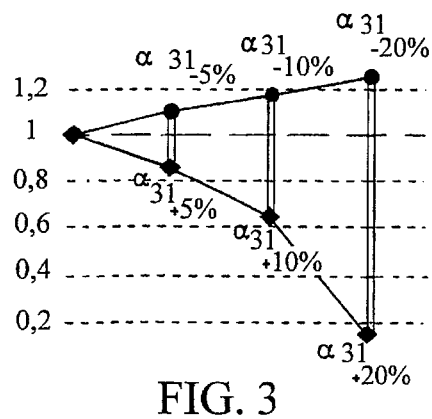
FIGS. 3 and 3a illustrate a signal parameter after rate alteration in accordance with different degrees of modulation or scanning points within the pulse interval in accordance with the principles of the present invention.

In the example according to FIGS. 2 and 3, the reference value field is formed by impedance measurement values, which have been detected using a type of modulation at different basic rates and degrees of modulation and different stress stages, so that a "two-dimensional" measurement value field is formed. It is also possible to select a "three-dimensional" measurement value field, for example an alterable type of modulation being used as an additional parameter.

In a further embodiment, instead of the alterable degrees of modulation, different scanning times may be detected within the pulse interval. The precision of the correlation analysis improves with the number of characteristic measurement values detected. This means that, in order to set up the measurement value sequence, either the number of degrees of modulation must be increased or the measurement values detected per degree of modulation must be increased. As it is more physiologically appropriate to keep the number and size of the degrees of modulation used as small as possible, in order to exceed the natural modulation range of the pulse frequency by as little as possible, use can be made of the fact that the stimulation propagation and pressure-volume function of the heart passes through four characteristic phases, each respectively specifically influenced by the frequency modulation. Accordingly it is appropriate, in the case of intracardial measurement values, which like the impedance are dependent on the pressure or volume configuration, to take at least two measurements per detected pulse interval, for example at the maximum during systole and at the minimum during distole.

Figure 6:
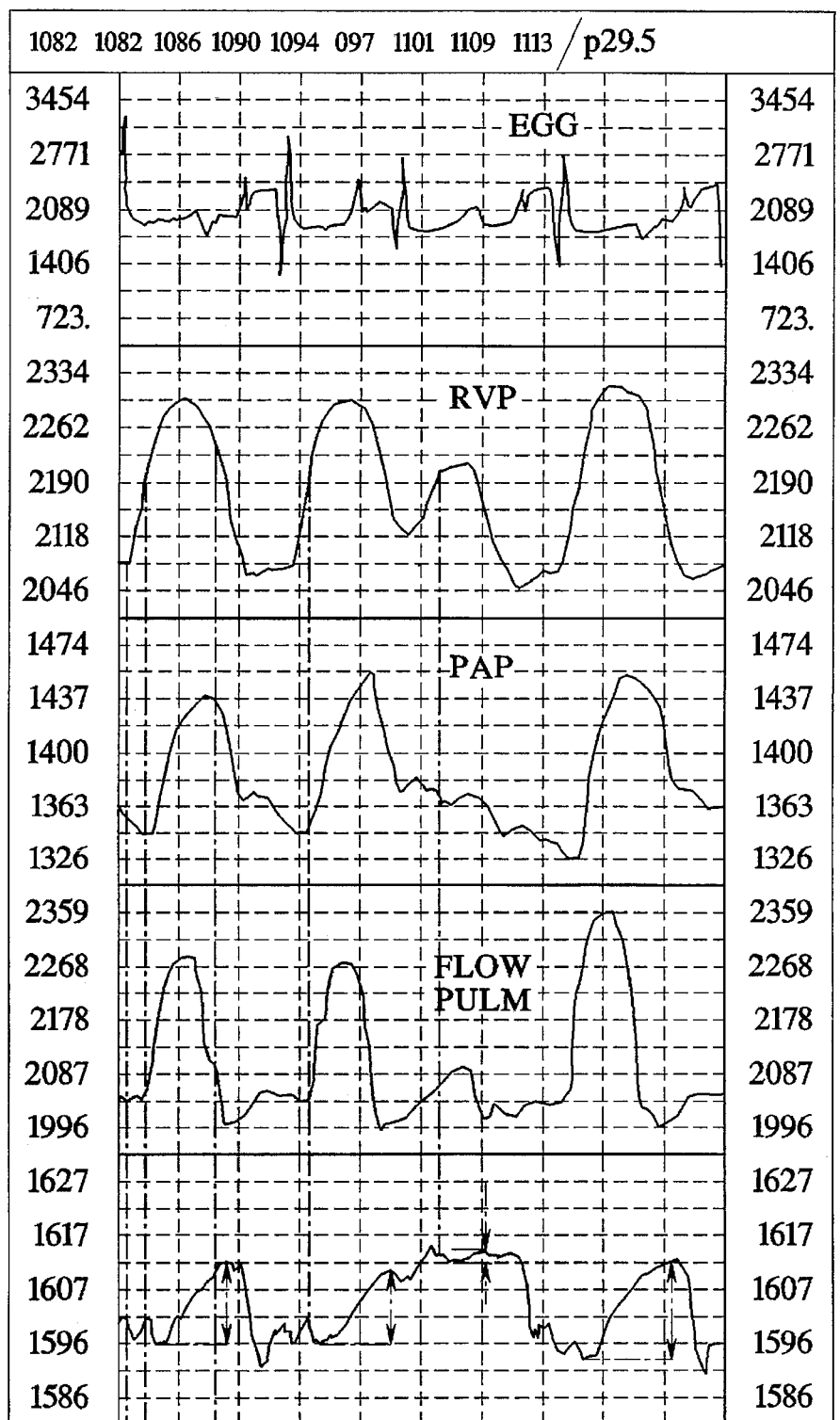
FIG. 6 shows characteristic curves of various intracardial signals for explaining the operation of the pacemakers of FIGS. 4 and 5.

FIG. 6 shows curves of different intracardial signals over the pulse interval of the heart period, and the four phase borders of the exertion time (isovolumetric contraction), the expulsion time, the relaxation time. (isovolumetric relaxation) and the filling time are marked on the X-axis. The curves show from the top downwards different types of intracardial signals, i.e. the ECG (EEG), the right-ventricular pressure (PAP, the pulmonary flow (flow pulm) and the right-ventricular impedance.

Scanning time points and duration can be chosen during the cardiac cycle or during the pulse interval at which the individual types of signals, depending on the type of modulation and the degree of modulation, exhibit an identifiable configuration. The scanning times may be different for the different types of signals.

In practice it is more advantageous to circumvent the outlay for a pulse phase-specific scanning, and instead to scan the measurement signal at strictly defined points in time during the pulse interval.

Figure 3A:
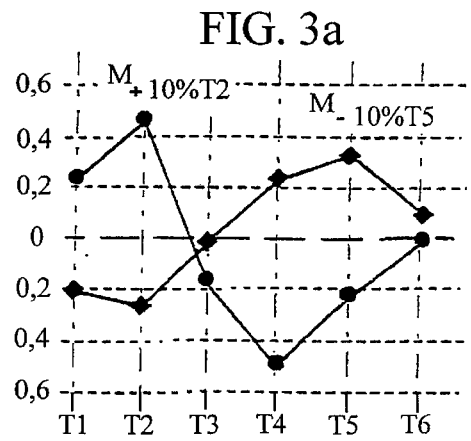

If the rate modulation is carried out with a degree of modulation of only, for example, ±10%, but six scanning points are used within the pulse interval, there results, similarly to FIG. 3, the measurement value sequence according to FIG. 3a.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable cardiac pacemaker comprising:

a pulse generator which emits successive stimulation pulses at a stimulation rate with said pulses respectively separated by a pulse interval;

electrode means, adapted for in vivo interaction with cardiac tissue, connected to said pulse generator for delivering said stimulation pulses to cardiac tissue, and comprising means for detecting a non-mechanical physiological characteristic indicative of cardiac demand and generating a cardiac demand-indicative signal corresponding thereto;

regulator means, connected to said pulse generator, for setting and changing the pulse interval of said stimulation pulses emitted by said pulse generator and thereby setting and changing said stimulation rate;

control means, connected to said regulator means, for causing said regulator means to modulate said stimulation rate in a plurality of modulation sequences, each modulation sequence starting from a different base stimulation rate;

processing means, connected to said electrode means, for processing said cardiac demand-indicative signals for generating a reference field consisting of a plurality of reference sequences of said cardiac demand-indicative signals respectively obtained with a patient in whom said cardiac pacemaker is implanted experiencing different levels of physical stress with at least one sequence of said cardiac demand-indicative signals being obtained during each modulation sequence for each different level of physical stress;

storage means for storing said reference field; and comparator means, connected to said processing means, said storage means and said regulator means, for, after said reference field is generated and stored, comparing a current sequence of said cardiac demand-indicative signals to each of said reference sequences in said reference field for identifying a highest correlating reference sequence in said reference field with which said current sequence has a highest correlation, and for commanding said regulator means to set a pulse interval to cause said pulse generator to emit said stimulation pulses at a stimulation rate equal to the basic stimulation rate of the modulation sequence which produced said highest correlating reference sequence.

2. An implantable cardiac pacemaker as claimed in claim 1 wherein said control means comprises means for controlling said regulator means for modulating said stimulation rate with at least one modulation type and a plurality of different degrees of modulation within said at least one modulation type and for controlling said processing means for obtaining cardiac demand-indicative signals respectively comprising each reference sequence at each of said different degrees of modulation.

3. An implantable cardiac pacemaker as claimed in claim 1 wherein said control means comprises means for controlling said regulator means for modulating said stimulation rate with at least one type of modulation of said stimulation rate and at least one modulation degree and for controlling said processing means for obtaining cardiac demand-indicative signals respectively comprising each reference sequence at successive times within a pulse interval.

4. An implantable cardiac pacemaker as claimed in claim 1 wherein said regulator means comprises means for modulating said stimulation rate by shortening the pulse interval between only two successive stimulation pulses with respect to a basic pulse interval defined by said basic stimulation rate, and for periodically repeating the shortening of said pulse interval between only two successive stimulation pulses after each occurrence of a predetermined number of said stimulation pulses.

5. An implantable cardiac pacemaker as claimed in claim 1 wherein said regulator means comprises means for modulating said stimulation rate by lengthening the pulse interval between only two successive stimulation pulses with respect to a basic pulse interval defined by said basic stimulation rate, and for periodically repeating the lengthening of said pulse interval between only two successive stimulation pulses after each occurrence of a predetermined number of said stimulation pulses.

6. An implantable cardiac pacemaker as claimed in claim 1 wherein said means for detecting a non-mechanical physiological characteristic indicative of cardiac demand comprises means for detecting a non-mechanical physiological characteristic indicative of cardiac demand includes two electrodes and comprises means for detecting said non-mechanical physiological characteristic indicative of cardiac demand without application of current between said two electrodes.

7. An implantable cardiac pacemaker as claimed in claim 6 wherein said means for detecting said non-mechanical physiological characteristic indicative of cardiac demand without application of current between said two electrodes comprises means for detecting an electrocardiogram.

8. An implantable cardiac pacemaker as claimed in claim 1 wherein said means for detecting a non-mechanical physiological characteristic indicative of cardiac demand comprises means for detecting a non-mechanical physiological characteristic indicative of cardiac demand includes two electrodes and comprises means for detecting said non-mechanical physiological characteristic indicative of cardiac demand with application of current between said two electrodes.

9. An implantable cardiac pacemaker as claimed in claim 8 wherein said means for detecting said non-mechanical physiological characteristic indicative of cardiac demand with application of current between said two electrodes comprises means for detecting an impedance.

10. An implantable cardiac pacemaker as claimed in claim 1 wherein said processing means comprises means for acquiring signals comprising said cardiac demand-indicative signals which are an extreme value of said non-mechanical physiological characteristic during systole of the heart of said patient.

11. An implantable cardiac pacemaker as claimed in claim 1 wherein said processing means comprises means for acquiring signals comprising said cardiac demand-indicative signals which are an extreme value of said non-mechanical physiological characteristic during diastole of the heart of said patient.

12. An implantable cardiac pacemaker as claimed in claim 1 wherein said processing means comprises means for acquiring signals comprising said cardiac demand-indicative signals which are a first derivative of an extreme value of said non-mechanical physiological characteristic during systole of the heart of said patient.

13. An implantable cardiac pacemaker as claimed in claim 1 wherein said processing means comprises means for acquiring signals comprising said cardiac demand-indicative signals which are a first derivative of an extreme value of said non-mechanical physiological characteristic during diastole of the heart of said patient.

14. An implantable cardiac pacemaker as claimed in claim 1 wherein said processing means comprises means for obtaining signals comprising said cardiac demand-indicative signals constituting a time interval between a start of a stimulation pulse and a subsequent occurrence, before a next stimulation pulse, of an extreme value of said non-mechanical physiological characteristic.

15. An implantable cardiac pacemaker as claimed in claim 1 wherein said cardiac demand-indicative signals each include an identifiable parameter of said non-mechanical physiological characteristic, wherein said control means comprises means for causing said regulator means to modulate said stimulation rate in one pulse interval, and wherein said processing means comprises means for identifying an alteration of said parameter occurring in at least one of two pulse intervals immediately following the pulse interval in which said stimulation rate was modulated and for generating said reference sequences from said alteration.

16. An implantable cardiac pacemaker as claimed in claim 15 wherein said processing means further comprises means for normalizing each alteration with respect to said parameter in said pulse interval in which said modulation occurred.

17. An implantable cardiac pacemaker as claimed in claim 1 wherein said cardiac demand-indicative signals each include an identifiable parameter of said non-mechanical physiological characteristic, wherein said control means comprises means for causing said regulator means to modulate said stimulation rate in one pulse interval, and wherein said processing means comprises means for obtaining an average value of alterations of said parameter respectively occurring in pulse intervals successively following the pulse interval in which said modulation occurred, and for generating said reference sequences from said average.

18. An implantable cardiac pacemaker as claimed in claim 1 wherein said control means comprises means for controlling said regulator means for modulating said stimulation rate according to a plurality of different types of modulation, and wherein said processing means comprises means for generating a plurality of reference fields, with one reference field being obtained for each modulation type, and wherein said storage means comprises means for storing said plurality of reference fields.

19. An implantable cardiac pacemaker as claimed in claim 1 further comprising means for detecting a physiological characteristic of said patient, other than said non-mechanical physiological characteristic, and wherein said control means comprises means for causing said regulator means to set said stimulation rate dependent on said physiological characteristic other than said non-mechanical physiological characteristic.

20. An implantable cardiac pacemaker as claimed in claim 19 wherein said means for detecting a physiological characteristic of said patient other than said non-mechanical physiological characteristic comprises means for detecting body movement of said patient.

21. An implantable cardiac pacemaker as claimed in claim 20 wherein said processing means comprises means for setting a stimulation rate dependent on body movement only if said stimulation rate dependent on body movement is consistent with said stimulation rate equal to the basic stimulation rate of the modulation sequence which produced said highest correlating reference sequence.

22. A method for pacing a heart comprising the steps of:
emitting successive stimulation pulses at a stimulation rate with said pulses respectively separated by a pulse interval;
delivering said stimulation pulses to cardiac tissue;
detecting a non-mechanical physiological characteristic indicative of cardiac demand and generating a cardiac demand-indicative signal corresponding thereto;
modulating said stimulation rate in a plurality of modulation sequences, each modulation sequence starting from a different base stimulation rate;
generating a reference field consisting of a plurality of reference sequences of said cardiac demand-indicative signals respectively obtained with a patient in whom said cardiac pacemaker is implanted experiencing different levels of physical stress with at least one sequence of said cardiac demand-indicative signals being obtained during each modulation sequence for each different level of physical stress;
storing said reference field; and
after said reference field is generated and stored, comparing a current sequence of said cardiac demand-indicative signals to each of said reference sequences in said reference field for identifying a highest correlating reference sequence in said reference field with which said current sequence has a highest correlation, and setting a pulse interval for emitting said stimulation pulses at a stimulation rate equal to the basic stimulation rate of the modulation sequence which produced said highest correlating reference sequence.

23. A method as claimed in claim 22 wherein the steps of modulating said stimulation rate comprises modulating said stimulation rate with at least one modulation type and a plurality of different degrees of modulation within said at least one modulation type and wherein the steps of generating a reference field includes obtaining cardiac demand-indicative signals respectively comprising each reference sequence at each of said different degrees of modulation.

24. A method as claimed in claim 22 wherein the step of modulating said stimulating rate comprises modulating said stimulation rate with at least one type of modulation of said stimulation rate and at least one modulation degree and wherein the step of generating a reference field includes obtaining cardiac demand-indicative signals respectively comprising each reference sequence at successive times within a pulse interval.

25. A method as claimed in claim 22 wherein the steps of modulating said stimulation rate comprises modulating said stimulation rate by shortening the pulse interval between only two successive stimulation pulses with respect to a basic pulse interval defined by said basic stimulation rate, and periodically repeating the shortening of said pulse interval between only two successive stimulation pulses after each occurrence of a predetermined number of said stimulation pulses.

26. A method as claimed in claim 22 wherein the step of modulating said stimulation rate comprises modulating said stimulation rate by lengthening the pulse interval between only two successive stimulation pulses with respect to a basic pulse interval defined by said basic stimulation rate, and periodically repeating the lengthening of said pulse interval between only two successive stimulation pulses after each occurrence of a predetermined number of said stimulation pulses.

27. A method as claimed in claim 22 wherein the step of detecting a non-mechanical physiological characteristic indicative of cardiac demand comprises detecting a non-mechanical physiological characteristic indicative of cardiac demand using two electrodes without application of current between said two electrodes.

28. A method as claimed in claim 27 wherein the step of detecting said non-mechanical physiological characteristic indicative of cardiac demand without application of current between said two electrodes comprises means for detecting an electrocardiogram.

29. A method as claimed in claim 22 wherein the step of detecting a non-mechanical physiological characteristic indicative of cardiac demand comprises detecting a non-mechanical physiological characteristic indicative of cardiac demand using two electrodes with application of current between said two electrodes.

30. A method as claimed in claim 29 wherein the step of detecting said non-mechanical physiological characteristic indicative of cardiac demand with application of current between said two electrodes comprises detecting an impedance.

31. A method as claimed in claim 22 wherein the step of generating a reference field comprises acquiring signals comprising said cardiac demand-indicative signals which are an extreme value of said non-mechanical physiological characteristic during systole of the heart of said patient.

32. A method as claimed in claim 22 wherein the step of generating a reference field comprises acquiring signals comprising said cardiac demand-indicative signals which are an extreme value of said non-mechanical physiological characteristic during diastole of the heart of said patient.

33. A method as claimed in claim 22 wherein the step of generating a reference field comprises acquiring signals comprising said cardiac demand-indicative signals which are a first derivative of an extreme value of said non-mechanical physiological characteristic during systole of the heart of said patient.

34. A method as claimed in claim 22 wherein the step of generating a reference field comprises acquiring signals comprising said cardiac demand-indicative signals which are a first derivative of an extreme value of said non-mechanical physiological characteristic during aliastole of the heart of said patient.

35. A method as claimed in claim 22 wherein the step of generating a reference field comprises obtaining signals comprising said cardiac demand-indicative signals constituting a time interval between a start of a stimulation pulse and a subsequent occurrence, before a next stimulation pulse, of an extreme value of said non-mechanical physiological characteristic.

36. A method as claimed in claim 22 wherein said cardiac demand-indicative signals each include an identifiable parameter of said non-mechanical physiological characteristic, wherein the step of modulating the stimulation rate comprises modulating said stimulation rate in one pulse interval, and wherein the step of generating a reference field comprises identifying an alteration of said parameter occurring in at least one of two pulse intervals immediately following the pulse interval in which said stimulation rate was modulated and generating said reference sequences from said alteration.

37. A method as claimed in claim 36 wherein the step of generating a reference field comprises normalizing each alteration with respect to said parameter in said pulse interval in which said modulation occurred.

38. A method as claimed in claim 22 wherein said cardiac demand-indicative signals each include an identifiable parameter of said non-mechanical physiological characteristic, wherein the step of modulating the stimulation rate comprises modulating said stimulation rate in one pulse interval, and wherein the step of generating a reference field comprises obtaining an average value of alterations of said parameter respectively occurring in pulse intervals successively following the pulse interval in which said modulation occurred, and generating said reference sequences from said average.

39. A method as claimed in claim 22 wherein the step of modulating the stimulation rate comprises modulating said stimulation rate according to a plurality of different types of modulation, and wherein the step of generating a reference field comprises generating a plurality of reference fields, with one reference field being obtained for each modulation type, and wherein the step of storing said reference field comprises storing said plurality of reference fields.

40. A method as claimed in claim 22 comprising the additional steps of detecting a physiological characteristic of said patient, other than said non-mechanical physiological characteristic, and setting said stimulation rate dependent on said physiological characteristic other than said non-mechanical physiological characteristic.

41. An implantable cardiac pacemaker as claimed in claim 40 wherein the step of detecting a physiological characteristic of said patient other than said non-mechanical physiological characteristic comprises detecting body movement of said patient.

42. A method as claimed in claim 41 wherein the step of setting said stimulation rate comprises setting said stimulation rate dependent on body movement only if said stimulation rate dependent on body movement is consistent with said stimulation rate equal to the basic stimulation rate of the modulation sequence which produced said highest correlating reference sequence.

* * * * *